(12) United States Patent
Boechat et al.

(10) Patent No.: US 8,071,777 B2
(45) Date of Patent: Dec. 6, 2011

(54) COMPOUNDS DERIVED FROM ARTESUNATE, PREPARATION PROCESS, PHARMACEUTICAL COMPOSITION AND USE OF THE RESPECTIVE MEDICINE

(75) Inventors: Núbia Boechat, Niterói (BR); Marcus Vinicius Nora de Souza, Minas Gerais (BR); Alessandra Leda Valverde, Rio de Janeiro (BR); Antoniana Ursine Krettli, Minas Gerais (BR)

(73) Assignee: Fundação Oswaldo Cruz - FIOCRUZ, Rio de Janeiro (BR)

( * ) Notice: Subject to any disclaimer, the term of this patent is extended or adjusted under 35 U.S.C. 154(b) by 989 days.

(21) Appl. No.: 11/578,530

(22) PCT Filed: Apr. 12, 2005

(86) PCT No.: PCT/BR2005/000049
§ 371 (c)(1), (2), (4) Date: Jul. 25, 2007

(87) PCT Pub. No.: WO2005/100370
PCT Pub. Date: Oct. 27, 2005

(65) Prior Publication Data
US 2007/0281968 A1 Dec. 6, 2007

(30) Foreign Application Priority Data
Apr. 13, 2004 (BR) ...................................... 0401107

(51) Int. Cl.
*C07D 215/38* (2006.01)
*A61K 31/04* (2006.01)

(52) U.S. Cl. .......................... 546/159; 546/163; 514/312
(58) Field of Classification Search .................. 546/159, 546/163; 514/312
See application file for complete search history.

(56) References Cited

FOREIGN PATENT DOCUMENTS
EP 0362810 * 4/1990

OTHER PUBLICATIONS

Angus, Antimicrobial Agents and Chemotherapy, Mar. 2002, pp. 778-782.*
de Pilla Varotti, AntiMic Agents and Chemo, Vov 2008, vol. 52(11), pp. 3868-3874.*
Herwaldt, Antimic Agents and Chemo, Jul. 1988, pp. 953-956, vol. 32(7).*
Wetsteyn, Br J Clin Pharmac, 1995, vol. 39, pp. 696-699.*
de Pilla Varotti, Antimic Agents and Chemo, vol. 52(11), pp. 3868-3874, Nov 2008.*
Herwaidt, Antimic Agents and Chemo, Jul. 1988, pp. 953-956, vol. 32(7).*
Wetsteyn, Br J Clin Pharmac, vol. 39, pp. 696-699, 1995.*

* cited by examiner

*Primary Examiner* — D M Seaman
(74) *Attorney, Agent, or Firm* — Klarquist Sparkman, LLP.

(57) ABSTRACT

The present invention refers to new compounds derived from artesunate salts with quinolines represented by the general formula (I) where X is represented by the general formula (II) and Y is represented by the general formula (III) depending on the radicals substituted in X (formula II), the relation X to Y (formula III) may vary from 1:1 to 1:7, because the amount of Y depends on the amount of N available in X for the formation of the salt. The radicals $R_1$, $R_2$, $R_3$, $R_4$, $R_5$, e $R^6$ in the general formula (II) are represented by: $R_1$=H, $CF_3$, $CH_3$, $OCH_3$, $NH_2$, halogen; $R_2$=H, $CH_3$, $NH_2$, halogen, NH—$CHCH_3(CH_2)_3N(C_2H_5)(CH_2CH_2OH)$, CH(OH)-2 (C5H$_{11}$N), NH—$R_7$—N—(C2H5)$_2$; $R_3$=H, m-$OC_6H_4CF_3$, $NH_2$; $R_4$=H, $CH_3$, $OCH_3$, $NH_2$, halogen; $R_5$=H, $CH_3$, $CF_3$, $NH_2$, halogen; $R_6$=H, $CF_3$, $CH_3$, $NH_2$, halogen, NH—$R_8$—N—$(C_2H_5)_2$, NHCH$(CH_3)(CH_2)_3NH_2$; $R_7$=$(CH_2)_2$, $(CH_2)_3$, $CHCH_3CH_2$, $(CH_2)_4$, $(CH_2)_5$, $CHCH_3(CH_2)_3$ $(CH_2)_6$, $(CH_2)_8$, $(CH_2)_{10}$, $(CH_2)_{12}$; $R_8$=$CHCH_3(CH_2)_3$, $CHCH_3(CH_2)CHCH_3$, $(CH_2)_2$, $(CH_2)_3$, $(CH_2)_6$, $(CH_2)_3O$ $(CH_2)_3$. The present invention also refers to a process of preparation of these general formula (I) compounds, and the pharmaceutical compositions, in which these compounds are included especially their use as medicine for treatment or prevention or inhibition of malaria or other parasitic diseases such as: kaodzera, Chagas disease, leishmaniasis, amoebiasis, giardiasis, trichommoniasis, toxoplasmosis, schistosomiasis, as well as other helminthiases.

17 Claims, No Drawings

COMPOUNDS DERIVED FROM ARTESUNATE, PREPARATION PROCESS, PHARMACEUTICAL COMPOSITION AND USE OF THE RESPECTIVE MEDICINE

CROSS REFERENCE TO RELATED APPLICATIONS

This is the U.S. National Stage of International Application No. PCT/BR2005/000049, filed Apr. 12, 2005, which was published in English under PCT Article 21(2), and claims benefit of priority of Brazilian Patent Application No. PI 0401107-4, filed Apr. 13, 2004, which is incorporated herein in its entirety.

The present invention refers to new compounds derived from artesunate salts with quinolines represented by the general formula I:

$$X^+ \cdot Y^-$$

where X is represented by the general formula II:

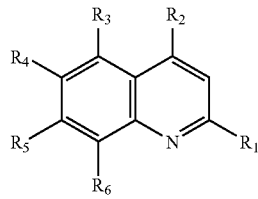

and Y is represented by the general formula III:

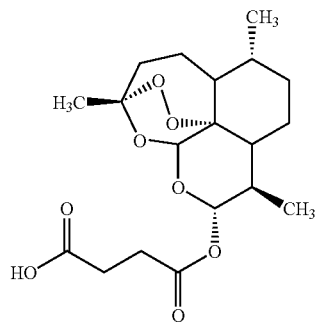

Depending on the radicals substituted in X (formula II), the relation X to Y (formula III) may vary from 1:1 to 1:7, because the amount of Y depends on the amount of N available in X for the formation of the salt.

The radicals $R_1$, $R_2$, $R_3$, $R_4$, $R_5$ e $R_6$ in the general formula II are represented by:

$R_1$=H, $CF_3$, $CH_3$, $OCH_3$, $NH_2$, halogen;
$R_2$=H, $CH_3$, $NH_2$, halogen, NH—$CHCH_3(CH_2)_3N(C_2H_5)$ ($CH_2CH_2OH$), CH(OH)-2-($C_5H_{11}N$), NH—$R_7$—N—(C2H5)$_2$;
$R_3$=H, M-$OC_6H_4CF_3$, $NH_2$;
$R_4$=H, $CH_3$, $OCH_3$, $NH_2$, halogen;
$R_5$=H, $CH_3$, $CF_3$, $NH_2$, halogen;
$R_6$=H, $CF_3$, $CH_3$, $NH_2$, halogen, NH—$R_8$—N—$(C_2H_5)_2$, $NHCH(CH_3)(CH_2)_3NH_2$;
$R_7$=$(CH_2)_2$, $(CH_2)_3$, $CHCH_3CH_2$, $(CH_2)_4$, $(CH_2)_5$, $CHCH_3$ $(CH_2)_3$, $(CH_2)_6$, $(CH_2)_8$, $(CH_2)_{10}$, $(CH_2)_{12}$;
$R_8$=$CHCH_3(CH_2)_3$, $CHCH_3(CH_2)CHCH_3$, $(CH_2)_2$, $(CH_2)_3$, $(CH_2)_6$, $(CH_2)_3O(CH_2)_3$.

The present invention also refers to a process of preparation of these general formula I compounds, and the pharmaceutical compositions containing said compounds, and especially their use as medicine for treatment or prevention or inhibition of malaria or other parasitic diseases such as: kaodzera, Chagas' disease, leishmaniasis, amoebiasis, giardiasis, trichomoniasis, toxoplasmosis, schistosomiasis, as well as other helminthiases. Moreover, the present invention provides a method of treatment, prevention or inhibition of malaria or other parasitic diseases, including the use of a therapeutic effective amount of a general formula I compound for the human being, who needs the referred treatment, prevention or inhibition.

BACKGROUND OF THE INVENTION

Malaria, also called maleita, palustre fever, impaludism, terçã fever or sezão, is a parasitic disease that, according to data from World Health Organization, affects about 300 million people in the world. It is considered to be, besides Aids, a world health problem. Malaria causes approximately 1 to 1.5 million deaths a year. It is one of the most important health problems nowadays, since its transmission occurs in almost 100 countries, in tropical and subtropical regions, inhabited by more than one third of the world population.

The distribution of the risk of malaria acquisition is not uniform within the same country and it is often unequal in areas situated in the same region, in addition, it is variable according to the seasons of the year and as time passes. In general, the risk is high in Africa (sub-Saharian area), South America (Amazon basin), Irian Jaia, Madagascar, Papua New Guine, Southeast Asia and Vanuatu. It is sort of low in Afghanistan (East), Central America, South America (except in the Amazon basin), North America (rural areas of Mexico), China (north), Egypt, India, Indonesia, Iraq, Iran, Malaysia, Sri Lanka, South Iraq, Middle East, Paquistan and Arabian peninsula (southeast). In Africa there are 90% of the cases of malaria, affecting, most of all, children under five years old, especially those who live in distant rural areas with little health assistance available. Malaria is endemic in Brazil where, annually, more than 400 thousand infected people are registered, the majority in the Amazon region.

Malaria is caused by a protozoan genus *Plasmodium*, which has about 100 species. Among these species only four of them affect humans, *P. vivax*, responsible for 80% of the current cases in Brazil, *P. malariae* which hardly ever occurs, *P. falciparum* responsible for a lethal and serious malaria if not rapidly and correctly treated, and *P. ovale*, not present in Brazil. Malaria is transmitted to mammals by insects: order Diptera, family Culicidae, and genus *Anopheles*. This genus comprehends about 400 species, but only a reduced number are important to the epidemiology of malaria in each region. In Brazil, five species are considered to be the main vectors: *Anopheles darlingi, A. aquasalis, A. albitarsis, A. cruzi* and *A. bellator*.

The parasite is transmitted by the bite of the infected insect that innoculates the sporozoans, which get lodged in the hepatic tissue, when it comes to the human *Plasmodium*, they multiply intensively (a sporozoan generates from 10 thousand to 40 thousand schizonts within the hepatocyte). Released from the host cell, the parasites fall into the blood stream, invading and multiplying themselves in the red cells, provoking clinical manifestations of the disease, mainly intermittent fever, chronic headache, myalgia, anemia, breathing difficulties, convulsions and coma. In some regions of Africa a serious anemia is the common cause of infant mortality for some reason or another.

There are many classes of active antimalarial medicines against blood forms of the parasite. Among the more used antimalarials are: (a) the antifolates type I and II (e.g. pyrimethamine and sulfadoxine), which inhibit the parasite dihydrofolate reductase; (b) the aminoquinolines (e.g. chloroquine and amodiaquine); (c) the artemisinin derivatives (e.g. artesunate and arteeter) have as their most important site of action the digestive vacuole of the parasite. Primaquine acts against the hepatic forms of slow development common in P. vivax and responsible for relapses.

In the last decades the use of some blood schizonticides, in determined areas, became inefficient due to the emergence of resistance to them. Resistance to chloroquine, detected initially in the 1960's in Magdalena Valley, Colombia, and later in Vietnam and Brazil, is widely spread and will continue to appear in new areas, as it happened in Africa in the 1980's. As a solution to this problem, it was used again the quinine, a drug with high toxicity, and mefloquine, described by the American Armed Forces based on a selection of thousand of drugs derived from chloroquine. It was believed that mefloquine was a medicine 100% efficient against chloroquine-resistent parasites. However, P. falciparum developed resistance to mefloquine very fast, this fact was first observed in 1990, as well as other drags commonly used. In the last 20 years, besides mefloquine, some drugs, such as halofantrine and artemisinin derivatives were developed to treat chloroquine-resistant P. falciparum.

The combination of drugs have been employed successfully in different classes of diseases, AIDS, cancer, and tuberculosis, for instance. This strategy of combination of drugs has also been employed with promising results against malaria. As an example, it can be cited the combination of artemisin derivatives with lumefantrine or doxycycline, as well as the combination of mefloquine with tetracycline or doxycycline (Wilairatana, P. et al. *Archives of Medical Research*, 2002, 33, 416). The combination of quinine and Fansidar (pyrimethamine and sulfadoxine) is employed to treat chloroquine-resistant P. falciparum.

It is known that suppositories of artesunate provide fast response to fighting the parasite and fever in severe cases of P. Falciparum; however, the recrudescence rate is high. Mefloquine (1250 mg) is administered in order to prevent and reduce recrudescence [Looareeswan et al., Ann. Trop. Méd. Parasitol. 89, 1995, 469-475; Looareeswan et al., Jpn. J. Trop. Med. Hyg. 24 (Suppl. 1) 1996, 13-15].

However, as for the presence of multidrug-resistent P. Falciparum in many countries, the treatment of malaria with the drugs available nowadays is not always effective, the same happens to the chemoprophylaxis, not used in Brazil anymore.

It is noticed through patent documents WO9425436 and WO02083641, that researches are being done in order to obtain amino derivatives. In the document WO02083641 these compounds may be combined with antimalarial compounds, such as quinolines (mefloquine) and antimalarial peroxides (artesunate).

This form of treatment, in which is used more than one medicine active in malaria treatment, even if one of them is new as previously reported, is susceptible of failure due to the resistance developed by the P. falciparum in relation to well-known drugs.

Hence, according to the increase in the resistance of this parasite, the research is absolutely necessary to develop new chemotherapeutic agents capable of fighting malaria effectively, which tends to aggravate with the planet global warmth and the deteriorating health system in many countries in tropic regions, where the disease is endemic.

The artesunate was developed in 1982 in China and the mefloquine in 1971, in the USA. According to what was previously presented, it is applied a combination of antimalarial drugs or polytherapy, e.g. the use of mefloquine and artesunate.

However, it has never been proposed to develop artesunate salts with quinolines, as it is described in the present invention, with antimalarial activity or against other diseases caused by other protozoans in order to overcome the difficulties pointed out. It is important to highlight that, since they are water soluble salts, the compounds of the invention allow a simplification in its formulation.

SUMMARY OF THE INVENTION

The objective of the present invention is to provide new compounds derived from artesunate salts with general formula I quinolines.

Another objective of the present invention is the process or preparation of new compounds derived from artesunate salts with general formula I quinolines.

Another result brought out by the present invention is the new pharmaceutical composition comprising one of the new compounds derived from artesunate with general formula I quinolines and an acceptable pharmaceutical vehicle.

The present invention also aims at using new compounds derived from artesunate salts with general formula I quinolines for the treatment, prevention and inhibition of malaria or other parasitic diseases.

Another result of this invention is the method of treatment, prevention or inhibition of malaria or other parasitic diseases, comprising the administration of a therapeutically effective amount of a compound derived from artesunate salts with general formula I quinolines to the human being who needs the referred treatment, prevention or inhibition.

DESCRIPTION OF THE INVENTION

The present invention refers to new compounds derived from artesunate salts with quinolines represented by the general formula I:

$$X^+.Y^-$$

where X is represented by the general formula II:

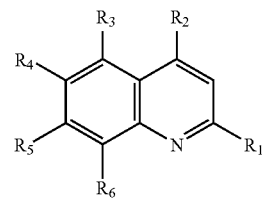

and Y represented by the general formula III:

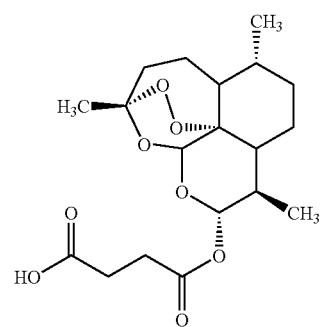

Depending on the radicals substituted in X (formula II), the relation X to Y (formula III) may vary from 1:1 to 1:7, because the amount of Y depends on the amount of N available in X for the formation of the salt.

The radicals $R_1$, $R_2$, $R_3$, $R_4$, $R_5$ e $R_6$ in the general formula II are represented by:

$R_1$=H, $CF_3$, $CH_3$, $OCH_3$, $NH_2$, halogen;
$R_2$=H, $CH_3$, $NH_2$, halogen, NH—$CHCH_3(CH_2)_3N(C_2H_5)(CH_2CH_2OH)$, $CH(OH)$-2-$(C_5H_{11}N)$, NH—$R_7$—N—$(C2H5)_2$;
$R_3$=H, m-$OC_6H_4CF_3$, $NH_2$;
$R_4$=H, $CH_3$, $OCH_3$, $NH_2$, halogen;
$R_5$=H, $CH_3$, $CF_3$, $NH_2$, halogen;
$R_6$=H, $CF_3$, $CH_3$, $NH_2$, halogen, NH—$R_8$—N—$(C_2H_5)_2$, $NHCH(CH_3)(CH_2)_3NH_2$;
$R_7$=$(CH_2)_2$, $(CH_2)_3$, $CHCH_3CH_2$, $(CH_2)_4$, $(CH_2)_5$, $CHCH_3(CH_2)_3$, $(CH_2)_6$, $(CH_2)_8$, $(CH_2)_{10}$, $(CH_2)_{12}$;
$R_8$=$CHCH_3(CH_2)_3$, $CHCH_3(CH_2)CHCH_3$, $(CH_2)_2$, $(CH_2)_3$, $(CH_2)_6$, $(CH_2)_3O(CH_2)_3$.

The new compounds derived from artesunate salts with quinolines, represented by the general formula I, present proven antimalarial activity, they may be employed in the treatment or prevention from diseases caused by a variety of protozoans.

Besides that, the compounds of the present invention have been of great advantage in terms of effectiveness when compared to a combination of drugs or polytherapy, as for example, the use of mefloquine and artesunate, the way it is known as the state of the art.

Administering more that one medicine active in the treatment of malaria, either in combination or polytherapy, is susceptible to failure because of the resistance developed by the *P. falciparum* to well-known drugs.

Another advantage of the compounds described in the current invention, represented by the general formula I, is the fact that they are more water soluble than mefloquine and artesunate, what allows the simplification of its formulation.

The present invention also refers to a simple and original process to obtain the derivatives of artesunate salts with quinolines represented by the general formula I.

The general process to prepare the compounds derived from artesunate salts and quinolines comprises the following stages:

a) solubilization of quinoline, represented by the general formula II, as a free base form in organic solvents;

b) solubilization of artesunate, represented by the general formula III, in organic solvents;

c) addition of the artesunate solution (stage b) to the quinoline solution (stage a) in order to obtain derivatives of artesunate salts of quinolines;

d) solvent evaporation for salt precipitation;

e) salt filtration in order to obtain derivatives of artesunate salts of quinolines as a solid product. Its effectiveness ranges from 80 to 96%.

When the quinoline becomes a salt it can be converted into quinoline base-free form through the following stages:

i) solubilization of quinoline salt in selected polar solvents such as water, water/aliphatic alcohol from $C_1$ to $C_6$ and ether;

ii) quinoline conversion into base-free salt, using a saturated aqueous solution of inorganic base;

iii) extraction of quinoline in base-free form using organic solvents;

iv) drying of the organic phase with desiccant agents;

v) organic solvent evaporation to obtain quinoline in its base-free form.

The stage (i) ether may be selected among diethylether, t-butylmethylether, tetrahydrofuran and 1,2-dimetoxyethane.

In the conversion of quinoline in base-free form, stage (ii), it is employed an inorganic base selected among sodium hydroxide, lithium hydroxide, potassium hydroxide, calcium hydroxide and sodium bicarbonate.

Among organic solvents used in the extraction of quinoline into a base-free drug form, stage (iii) as well as in the solubilization of quinolines and artesunate stages (a) and (b), respectively, it is employed ether, halogenide solvents and alcohol. Ether may be selected among The stage (i) ether may be selected among diethylether, t-butylmethylether, tetrahydrofuran and 1,2-dimetoxyethane. Halogenide Solvents may be dichlorometan and chloroform, and the alcohol may be an aliphatic alcohol from $C_1$ to $C_6$.

In the drying process of the organic phase (stage iv) the diseccant agents may be anhydrous sodium sulphate, anhydrous magnesium sulphate and calcium chloride.

The compounds of the current invention may be used mainly in the treatment or prevention from malaria or other parasitic diseases, such as, kaodzera, Chagas' disease, leishmaniasis, amoebiasis, giardiasis, trichomoniasis, toxoplasmosis, schistosomiasis, as well as other helminthiases.

The application of the compound of this invention in the treatment of prevention from these diseases, caused by a variety of protozoans, is evident to an expert in the field that recognizes a substantial structural homology and superposition of activity and particularity of the substrate among the enzymes of *P. falciparum* and another protozoan.

The pharmaceutical composition of the current invention comprises, as an active ingredient, an effective amount of one of the derivatives of artesunate salts with quinolines and an acceptable pharmaceutical vehicle.

The acceptable pharmaceutical vehicle must be any type of material, inert and non-toxic, to allow the formulation of the active ingredient, in order to permit its administration. These vehicles are well-known by the experts.

Pharmaceutical compositions comprising the compounds of the current invention may be administered through the digestive tract (orally or through the use of suppositories), or via parenteral (cutaneous or intracutaneous).

To be administered by mouth, the medicine may come in tablets, pills, capsules, emulsion, solution or suspension. The inactive components in this case comprise excipients, ligants, desintegrants, diluents, lubricants, etc.

Solid compositions include the active ingredient mixed with non-toxic excipients suitable to manufacture tablets, such as starch, lactose, certain types of carbonates e bicarbonates, phosphates, talc etc. The tablets may be coated or not, depending on the point of the gastrointestinal tract where the desintegration and the absorption of the drug must occur.

In case of suspensions or aqueous solutions, excipients such as methyl-cellulose, sodium alginate, acacia gum, lecytin etc and one or more additives, such as preservers, colorants, flavouring agents, thickners, polyols, saccharose, glucose etc may be used.

The medicine in the form of a suppository contains conventional excipients, water soluble or not, for example, polyethylene, glycols, fat (coccoa-butter) or mixtures of these substances, natural oils or hydrogenated oils, liquid or semi-liquid polyols, fatty acids (fat), waxes.

For parenteral (subcutaneous, intramuscular and intravenous) route of administration, the medicine must be injectable. The inactive components used in this case include acceptable parenteral diluents and solvents and other non-toxic components such as suspension agents, oils, water, polyols, alcohols, glycerines, vegetable oils, lecytins, liposomes etc.

The quantity of the active principle, which will be combined with the acceptable pharmaceutical vehicle, in order to produce the final dosage form will depend on the organism to be treated as well as on the chosen way to administer it. The active ingredient will preferably range from 0.1 to 99% of the formulation weight. The concentration of the active principle should be most of all within 0.25 and 99% of the formulation weight.

However, it must be clear that the specific level of the dose for any patient will depend on a variety of factors including the activity of the employed compound, age, body weight, general clinical picture, sex, diet, time and via of administration, excretion rate, combination with other drugs, resistance and severity of the disease to be treated.

The present invention is described in details through the examples presented below. It is necessary to point out that the invention is not limited to these examples but it also includes variations and modifications within the limits in which it works.

EXAMPLE 1

Compound represented by the general formula I $X^+.Y^-$, where $R_1=CF_3$; $R_2=CH(OH)-2-(C_5H_{11}N)$; $R_3=R_4=R_5=H$; $R_6=CF_3$; and the relation X to Y equals 1:1.

In order to obtain the derivative of artesunate salt with mefloquine, it is employed a solution of mefloquine hydrochloride (2.00 g) in 50 ml of water/methanol (8:3). Then, it is added to this solution the same volume of ethyl ether at room temperature and under constant agitation. After that, it is added sodium bicarbonate until the effervescence ceases. The two formed phases are separated. The organic phase is dried with anhydrous sodium sulphate and the evaporated solvent. It is obtained 1.48 g of base free, which is again solubilized in 40 ml of ethyl ether. 1.50 g of artesunate is added to this solution.

The reacting mixture is kept in agitation for one night, then it is observed a white solid formation which is filtered (2.38 g, returning 80%). $^1$H-RMN (400 MHz, c), δ: 8.73 (d, J=8.8 Hz, 1H); 8.40 (d, J=8.8 Hz, 1H); 8.08 (s, 1H); 7.93 (t, J=7.9 Hz, 1H); 5.66 (d, J=5.7 Hz, 1H); 5.55 (s, 1H); 5.43 (d, J=4.5 Hz, 1H); 2.48 (m, 4H, —COCH$_2$CH$_2$CO—); 1.28 (s, 3H); 0.89 (d, J=6.2 Hz, 3H) and 0.76 (d, J=7.1 Hz, 3H).

EXAMPLE 2

Compound represented by the general formula $X^+.Y^-$, where $R_1=H$; $R_2=NHCHCH_3(CH_2)_3N(C_2H_5)_2$; $R_3=R_4=R_6=H$; $R_5=Cl$; and the relation X to Y equals 1:1.

To obtain the referred salt of artesunate and chloroquine, it was performed the same procedure described in the example 1, starting from the chloroquine diphosphate. The salt was obtained with 86% of efficiency. $^1$H-RMN (200 MHz, MeOH-d$_4$), δ: 8.35 (d, J=6.0 Hz, 1H); 8.23 (d, J=10.0 Hz, 1H); 7.79 (d, J=2.0 Hz, 1H); 7.44 (dd, J=8.0 and 2.0 Hz, 1H); 6.64 (d, J=6.0 Hz, 1H); 5.70 (d, J=10.0 Hz, 1H); 5.42 (s, 1H); 1.36 (d, J=6.0 Hz, 3H); 1.33 (s, 3H); 1.23 (m, 6H); 0.93 (d, J=6.0 Hz, 3H) and 0.84 (d, J=6.0 Hz, 3H).

EXAMPLE 3

Compound represented by the general formula $X^+.Y^-$, where $R_1=R_2=R_3=R_5=H$; $R_4=OCH_3$; $R_6=NHCHCH_3(CH_2)_3NH_2$; and the relation X to Y equals 1:2.

The disalt of artesunate and primaquine was obtained performing the same procedure described in the example 1, starting from primaquine diphosphate. The disalt was obtained with 88% of efficiency. $^1$H-RMN (200 MHz, DMSO-d$_6$), δ: 8.52 (dd, J=4.0 and 2.0 Hz, 1H); 8.06 (dd, J=4.0 and 2.0 Hz, 1H); 7.41 (dd, J=10.0 and 5.0 Hz, 1H); 6.47 (d, J=2.0 Hz, 1H); 5.63 (d, J=10.0 Hz, 2H); 5.51 (s, 2H); 3.81 (s, 3H, OCH$_3$); 1.27 (s, 6H); 1.19 (d, J=6.0 Hz, 3H); 0.84 (d, J=6.0 Hz, 6H) and 0.74 (d, J=6.0 Hz, 6H).

EXAMPLE 4

Pharmacological Evaluation

The pharmacological evaluation of the compounds of the current invention, in order to prove the respective therapeutical efficiency, may be demonstrated in the following tests where 3 samples were used, labeled "A", "B" and "C", and all the tests were done with samples that followed the same codes. Sample "A" is constituted of salt of artesunate and mefloquine (compound of artesunate salt according to the current invention), sample "B" is constituted of artesunate, while sample "C" is represented by mefloquine. The description of the tests is done in 3 stages: methodology, results and conclusions.

Test Methodology

To evaluate the antimalarial activity the following tests were carried out in different experiments in vivo using groups of Swiss female albino mice, weighing between 18 and 22 g. These mice were innoculated with 100,000 red cells infected with strain NK 65 of *Plasmodium berghei* (cause of malaria in rodents) according to the scheme previously proposed (Peters et al., *Annals of Tropical Medicine and Parasitology*, 1993, 87, 547). After inoculating the parasite via intraperitoneal, the animals were divided at random into groups of five. The treatment of the mice were initiated the day after the inoculation, for 4 days in sequence, applying samples "A", "B" e "C" administered via oral. The different groups of mice, represented by groups treated and not treated (group control) were kept in the same conditions, in polyacetylene cages, water and ration was offered ad libitum. A group was treated with chloroquine, an antimalarial of reference. The development of the infection was verified in all groups through blood samples collected for parasitaemia on the 5th and 7th day after the infection, and the parasitaemia was measured based on double blind tests, in codified slides, in order to minimize occasional bias.

The tests in vitro to evaluate the antimalarial activity were carried out with *P. falciparum* cultivated in red cells in 10% of human serum, in slabs of 96 wells, using Rieckman et al's traditional method, modified by Carvalho et al. Braz J. Med. Biol. Research, 1991. The parasites were incubated for 72 hours in culture medium having samples "A", "B" and "C" in different dilutions in ideal atmospherical conditions at 37° C.; drugs and the culture medium was changed every 24 hours. After this period, blood samples were collected for evaluation of the activity of each compound. As to control wells with complete culture medium were maintained, but with no addition of drugs, and wells in which chloroquine was present in different tested concentrations in triplicate.

Obtained Results

Not only in vivo but also in vitro, the activity of drugs was evaluated in relation to the group control without any drugs. The results are shown in table 1.

TABLE 1

Antimalarial effect of samples "A" (salt of artesunate and mefloquine), "B" (artesunate) and "C" (mefloquine) with a dose of 12 mg/kg in mice infected by *Plasmodium berghei* and treated via oral for 4 dias in sequence.

| Sample | Average parasitaemia (%) ± SD on days (% Inhibition of parasitaemia)* | | Cumulative mortality on different days of infection | | | | |
|---|---|---|---|---|---|---|---|
| | 5° | 7° | 10° | 19° | 23° | 35° | 48° |
| A | 0 (100%) | 0 (100%) | 0 | 0 | 0 | 0 | 0 |
| B | 0 (100%) | 0 (100%) | 0 | 0 | 1 | 2 | 3 |
| C | 0 (100%) | 0 (100%) | 0 | 0 | 0 | 0 | 0 |
| Control not treated | 4.3 ± 2.6 | 23.6 ± 10.7 | 1 | 5 | 5 | 5 | 5 |

Sd = standard deviation of averages of 5 mice in each group.
*In relation to the group control not treated.

Not only the artesunate, but also the mefloquine and the new salt of artesunate with quinoline, tested with a dose of 12 mg/kg via oral suppressed 100% the acute parasi taemia of treated animals, in evaluations carried out on the 5th and 7$^{th}$ day after the infection. We usually follow the evolution of treatment for 30 days but the animals were anemic and mortality occurred in one of the groups, the one treated with sample "B" (which was later decoded as pure artesunate). Because of this, we restarted collecting new blood samples.

TABLE 2

Recrudescence of the parasitaemia in animals infected by *P. berghei* and treated with, sample "B" (pure artesunate in a dose of 12 mg/kg).

| Sample | % Individual parasitaemia on different days | | | |
|---|---|---|---|---|
| | 30° | 33° | 36° | 48° |
| B | 0 | 0 | 0 | 0 |
| | 42 | 48 | † | |
| | 0.6 | 5 | 14 | 30 |
| | 24 | 40 | 53 | † |
| | † | | | |
| Average ± Sd | 16.6 ± 20.4 | 23.3 ± 24.3 | 33.5 ± 27.4 | 30 ± 21.2 |

Sd = standard deviation;
† = Animal death

Meanwhile groups treated with sample "A" (new compound, salt of mefloquine artesunate) and "C" (mefloquine) remained negative, the animals of the group treated with sample "B" (pure artesunate) showed recrudescency of the parasitaemia. Therefore, in animals treated with salt of artesunate with quinolines (sample "A") the cure of malaria was observed.

The results of tests in vitro with *P. falciparum* are depicted in Table 3 showing that artesunate and the salt of artesunate with quinolines presented similar activity in vitro, but higher than pure mefloquine. The variations observed in the activity of the compounds in these two different experiments are expected and take place due to limitations of the methodology which makes use of a microscopic for evaluations. This methodology is little accurate.

TABLE 3

Inhibiting concentrations (IC) approximated for the increasing of *P. falciparum* (W2) in vitro to the chloroquine (QC) and to samples "A", "B" and "C" against *P. falciparum*, in two distinct experiments.

| | IC in ng/ml | | | | | | | |
|---|---|---|---|---|---|---|---|---|
| | Experiment 1 | | | | Experiment 2 | | | |
| Sample | 40% | 50% | 80% | 95%-100% | 40% | 50% | 80% | 95%-100% |
| A | 0.83 | 1.03 | 1.85 | 4.07 | 0.46 | 0.8 | 1.5 | ≧5 |
| B | 0.37 | 0.46 | 0.99 | 1.54 | 0.33 | 0.43 | 1.3 | ≧5 |
| C | 0.93 | 1.24 | 12.9 | ≧50 | 2.8 | 3.4 | ≧5 | ≧5 |
| QC | 41.1 | 51.3 | 82.3 | 277.7 | 48.2 | 55.5 | 133.4 | ≧200 |

Artesunate and artesunate salt with quinolines demonstrated similar activities in vitro, while artesunate was not able to cure malaria in animals treated with a dose of 12 mg/kg. The best tested compound against malaria was the artesunate salt with quinolines.

The invention claimed is:

1. A compound derived from artesunate salts, characterized by the fact that it is represented by the general formula I:

$$X^+Y^-$$

where X is represented by the general formula II:

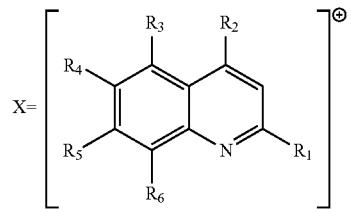

and Y is represented by the general formula III:

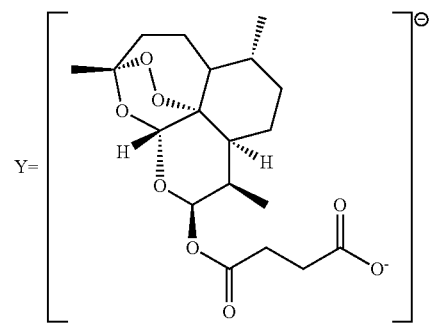

wherein $R_1$=CF3; $R_2$=CH(OH)-2-($C_5H_{11}N$); $R_3$=$R_4$=$R_5$=H and $R_6$=$CF_3$ and the relation X to Y equals 1:1.

2. Preparation process of an artesunate derived compound, as defined by claim 1, characterized by the fact it comprises the following stages:
   a) solubilization of quinoline, represented by the general formula II, as a free base form in organic solvents;
   b) solubilization of artesunate, represented by the general formula III, in organic solvents;
   c) addition of the artesunate solution (stage b) to the quinoline solution (stage a) in order to obtain derivatives of artesunate salts of quinolines;

d) solvent evaporation for salt precipitation;
e) salt filtration in order to obtain derivatives of artesunate salts of quinolines as a solid product. Its effectiveness ranges from 80 to 96%.

3. Preparation process of the artesunate derivative according to claim 2, characterized by the fact that base-free quinoline may be obtained through the following stages:
   i) solubilization of quinoline salt in selected polar solvents such as water, water/aliphatic alcohol from $C_1$ to $C_6$ and ether;
   ii) quinoline conversion into base-free salt, using a saturated aqueous solution of inorganic base;
   iii) extraction of quinoline in base-free form using organic solvents;
   iv) drying of the organic phase with desiccant agents;
   v) organic solvent evaporation to obtain quinoline in base-free form.

4. Preparation process of the artesunate derivative according to claim 3, characterized by the fact that stage (i) ether may be selected among diethylether, t-butylmethylether, tetrahydrofuran, and 1,2-dimetoxyethane.

5. Preparation process of the artesunate derivative according to claim 3, characterized by the fact that in the conversion of quinoline in its base-free form, stage (ii), it is employed an inorganic base selected among sodium hydroxide, lithium hydroxide, potassium hydroxide, calcium hydroxide, and sodium bicarbonate.

6. Preparation process of the compound derived from artesunate and quinolines according to claim 3 characterized by the fact that in the organic phase drying, stage (iv), desiccant agents may be selected among anhydrous sodium sulphate, anhydrous magnesium sulphate, and calcium chloride.

7. Preparation process of the compound derived from artesunate and quinolines according to claim 2 characterized by the fact that the organic solvents of stages (a), (b) and (iii) are selected among ethers, halogenide solvent and alcohols.

8. Preparation process of the compound derived from artesunate according to claim 7, characterized by the fact that ethers may be selected among diethylether, t-butylmethylether, tetrahydrofuran and 1,2-dimetoxyethano.

9. Preparation process of the compound derived from artesunate according to claim 7, characterized by the fact that halogenide solvents may be either dichlorometan or chloroform.

10. Preparation process of the compound derived from artesunate according to claim 7, characterized by the fact that alcohols may be aliphatic from $C_1$ to $C_6$.

11. Pharmaceutical composition characterized by an active ingredient, present in an effective amount of the derivative of artesunate salts with quinolines as defined in claim 1 and an acceptable pharmaceutical vehicle.

12. Pharmaceutical composition according to claim 11, characterized by the fact that the active ingredient ranges from 0.1 to 99% of composition weight.

13. Pharmaceutical composition according to claim 12, characterized by the fact that the active ingredient may in a concentration that ranges from 0.25 to 99% of the composition weight.

14. Pharmaceutical composition according to claim 13, characterized by the fact that it is employed in the treatment or prevention from malaria.

15. A method of treating, preventing, or inhibiting malaria characterized by administering a therapeutically effective amount of the general formula I compound of claim 1 for the human being, who needs treating, preventing, or inhibiting malaria.

16. A compound according to claim 1, characterized by the fact that the compounds are employed in the treatment or prevention from malaria.

17. The compound according to claim 1, wherein the general formula I compound is a more effective anti-malarial drug than the artesunate and quinolone components administered in combination as a polytherapy against drug-resistant *P. falciparum*.

\* \* \* \* \*